US012678525B2

(12) United States Patent
El-Ghazaly et al.

(10) Patent No.: US 12,678,525 B2
(45) Date of Patent: Jul. 14, 2026

(54) MICROWAVE-PLASMA DISINFECTOR (ORIGREEN)

(71) Applicant: BOARD OF TRUSTEES OF THE UNIVERSITY OF ARKANSAS, Little Rock, AR (US)

(72) Inventors: Samir El-Ghazaly, Fayetteville, AR (US); Amirreza Ghadimi Avval, Fayetteville, AR (US); Sara Ghayouraneh, Fayetteville, AR (US); Saleh Alfawaz, Fayetteville, AR (US); Ibrahim Alquaydheb, Fayetteville, AR (US)

(73) Assignee: Board of Trustees of the University of Arkansas, Little Rock, AR (US)

( * ) Notice: Subject to any disclaimer, the term of this patent is extended or adjusted under 35 U.S.C. 154(b) by 1051 days.

(21) Appl. No.: 17/853,804

(22) Filed: Jun. 29, 2022

(65) Prior Publication Data

US 2022/0409758 A1 Dec. 29, 2022

Related U.S. Application Data

(60) Provisional application No. 63/216,366, filed on Jun. 29, 2021.

(51) Int. Cl.
| | |
|---|---|
| *A61L 2/14* | (2006.01) |
| *A61L 2/12* | (2006.01) |
| *A61L 2/26* | (2006.01) |
| *H05H 1/00* | (2006.01) |

(52) U.S. Cl.
CPC .................................... *A61L 2/14* (2013.01); *A61L 2/12* (2013.01); *A61L 2/26* (2013.01); *H05H 1/01* (2021.05); *A61L 2202/11* (2013.01); *A61L 2202/14* (2013.01); *H05H 2245/36* (2021.05)

(58) Field of Classification Search
None
See application file for complete search history.

(56) References Cited

U.S. PATENT DOCUMENTS 11,097,022 B2 * 8/2021 Hancock .................. H05H 1/46

* cited by examiner

*Primary Examiner* — Brian W Cohen
*Assistant Examiner* — Nathanael Jason Downes
(74) *Attorney, Agent, or Firm* — Keith A. Vogt; Keith Vogt Ltd.

(57) ABSTRACT

A microwave-plasma disinfector (Origreen) with a microwave source with multi-feed points and variable output power. It also has a low-temperature atmospheric-pressure plasma source. This versatile microwave-plasma disinfector has the ability to decontaminate heat-sensitive materials by subjecting them to a microwave-assisted plasma with controlled microwave power. This dual-action, at suitable non-destructive microwave and plasma doses, sterilizes the equipment at a lower temperature with higher effectiveness than either plasma or microwaves alone

18 Claims, 14 Drawing Sheets

Power Distribution

Power Distribution

Power Distribution

Power Distribution

Power Distribution

4-Horns-2pp

Power Distribution

4-Horns-0pp

MICROWAVE-PLASMA DISINFECTOR (ORIGREEN)

RELATED APPLICATIONS

This application claims priority to U.S. Provisional Application No. 63/216,366, filed on Jun. 29, 2021, which is incorporated herein in its entirety.

STATEMENT REGARDING FEDERALLY SPONSORED RESEARCH & DEVELOPMENT

This invention was made with government support by the NSF grant 2033907. The government has certain rights in the invention.

Incorporation by Reference of Material Submitted on a Compact Disc

Not applicable.

BACKGROUND OF THE INVENTION

The topic of disinfection and sterilization of different materials and objects has been researched for many years. The main target in all of these studies is to clean the objects or materials from live pathogens and microorganisms. As is described by the Centers for Disease Control and Prevention (CDC), sterilization happens when 100% of the live pathogens on the objects and materials are cleaned, and when these live microorganisms are partially cleaned from the surface of materials and objects, the process is called disinfection. Hydrogen peroxide, chemical disinfectants, and autoclaves, in general, are the main disinfection and sterilization processes indicated by CDC.

There are a number of drawbacks associated with the widely used disinfection and sterilization processes. In the event of a pandemic or a natural disaster, there is always a shortage of chemical disinfectants and disposable PPE may be used for extended periods at the risk of exposing patients and medical staff to contamination. Moreover, additional risks arise from extended exposure to the chemical disinfectants and the inadvertently left residues on the protective gear have been identified as the stimulus for many diseases. In addition, any material or object to be disinfected such as PPE (e.g., masks, gloves, gowns, protective clothing, helmets, face shields, and goggles) must maintain their viability and features related to the shape, material, and form to be able to be reused after the disinfection process. There are also some long-term environmental effects from the over-consumption of these chemicals and some other techniques consume a great amount of energy. There are two other disinfection/sterilization techniques, namely plasma and microwave technologies, which have addressed the mentioned limitations with some of the already developed methods.

1) Plasma Technology

Plasma is a technology suitable for disinfection and sterilization applications. This topic has been thoroughly researched in recent years to analyze and demonstrate the microbicidal characteristics of plasma technology. From a temperature classification viewpoint, non-thermal plasma is a type of partially ionized gas with a lower temperature (~340 K) compared to thermal plasma (>1,000 K). Based on the fact that the non-thermal plasma is delivered at room temperature, it has minimal damaging effects on materials which makes it suitable for medical and biological applications. Several techniques, which are basically electrical discharge approaches, are used to generate this type of plasma. The techniques vary in the frequency of the power source used and the ambient gas pressure applied. Examples include micro-hollow cathode discharge (MHCD), atmospheric-pressure plasma jet (APPJ), and dielectric barrier discharge (DBD). They are all suitable for disinfecting medical devices with almost no impact on their structural arrangements.

In general, short processing times with low temperatures and without any associated chemical residues have made plasma technology a promising procedure for disinfection and sterilization. The effectiveness of plasma against a broad spectrum of microorganisms with a high level of resistance to chemical and physical treatments has already been studied and experimented. Although, according to the resistance hierarchy of the pathogens in response to inactivation by sterilization/disinfection processes, viruses such as HIV and COVID-19 are considered enveloped viruses which are highly susceptible in this regard. The interaction of plasma with the target cells is affected by the type of the working gas, treatment time, and the structure and size of the cell. Factors contributing to these interactions also include the charged particles, the reactive oxygen and nitrogen species, and UV radiation.

Regarding the disinfection processes, the non-thermal plasma gas at the atmospheric pressure level gives rise to multiple chemical and physical reactions due to the fact that it is an active material. At the first stage of the disinfection methodology by plasma, the pathogens and microorganisms are bombarded by neutral chemical species along with the ions and electrons present in the plasma, which results in the decomposition of their structural molecules. This process is sometimes facilitated by the oxidizing effects associated with the chemical species that are highly reactive. When the hydrogen bonds in the molecular structure of the pathogens are broken by the ions, the decomposed microorganisms become lighter and more volatile which assists in fast evaporation from the surface. The process of reduction in the number of germs and organic molecules is continued up to a point that the treated surface is completely sterilized.

Moreover, the reactive oxygen species are the chemically active oxygen molecules and ions present in the plasma matter. Alkyl radicals that are easily oxidized in the air are produced due to the reaction of the hydroxyl radicals with the microorganisms on the surface. Based on this mechanism, cell walls and bacteria capsules are damaged, which dominates the cell reparation process. As a powerful oxidant, ozone assists in this destruction process. Additionally, the DNA molecules of the cells are destroyed by the penetration of hydrogen peroxide into the nucleus of the microorganisms. These actions make the reactive oxygen species to be an effective mechanism for disinfecting the surfaces by plasma technology. Another group of species in the plasma is the nitrogen reactive molecules. Compared to their oxygen counterparts, these molecules are less reactive but possess sufficient lifetime to have an impact on the inner layers of the tissues. Ultraviolet radiation is another mechanism of disinfecting by plasma technology, which is not as effective compared to the above-mentioned mechanisms, but UV radiation with sufficient intensity expedites the destruction of the DNA molecules.

2) Microwave Technology

Microwaves are a type of electromagnetic waves with a frequency range between 0.3-300 GHz. Over the years, there has been a large number of publications and patents high-lighting the many applications of microwave devices in medical and industrial fields.

For medical purposes, microwaves have been widely used for the disinfection and sterilization of many objects such as glass, plastic surfaces, soft contact lenses, contaminated gauze, dental instruments, and liquids. In general, most microwave devices are utilized at a frequency of 2.45 GHz.

The critical concept in the operating mechanism of these devices is that the heating process happens in the form of energy conversion and is different from that of conventional heating. In an alternating electric field inside microwave devices, friction, caused by the created vibrations between water molecules, is produced. The heat is afterward generated as a result of this friction. However, the mechanisms of destruction in microwaves are not completely understood, and the researchers disagree as to whether it is the thermal or non-thermal effects that kill undesirable microorganisms and pathogens. One of the limitations associated with microwave disinfection is that the microwave absorbent materials exposed to the microwave field must be compatible with the amount of energy they receive. For instance, rubber cannot withstand relatively high temperatures and cannot be disinfected by microwaves. Moreover, some protective gear may have metallic inserts in them that would overheat and likely burn the material around them when exposed to the microwave powers needed for disinfection.

The microbicidal characteristics and the disinfecting actions of microwave technology on fungal cells, bacteria, and viruses are well established in the literature and are extensively demonstrated by early reports. The utilized microwaves in these processes were generally the so-called home-type microwaves and depending on the organism to be dealt with, the treatment time ranged between 1-5 minutes. More recent reports confirmed these results at the same operating frequency and treatment time and also mentioned that for sterilization purposes in high-power microwaves, the presence of water along with microwave absorbent materials is necessary. As a general rule, radiation powers ranging from 500 to 1500 watts are sufficient to sterilize surfaces contaminated with various microorganisms.

There are some reported challenges to the sterilization of medical devices with microwaves. The most common commercial microwave source is magnetron. Equipment based on this source, while inexpensive, has neither uniform nor homogeneous field strengths. This leads to an uneven distribution of microwave energy over the absorbent material which creates hot and cold spots. As a result, there may be areas that are not fully sterilized or disinfected. Additionally, some of the produced energy by microwaves may not be absorbed and reflects back to the energy source. The microwave source may not withstand high levels of reflected energy for long periods, and this may damage the source.

BRIEF SUMMARY OF THE INVENTION

In one embodiment, the present invention concerns a disinfector that depends in its operation on both microwaves and plasma. The microwave-plasma disinfector (Origreen) is similar in functionality to conventional autoclaves or microwave ovens. It has a microwave source with multi-feed points and variable output power. It also has a low-temperature atmospheric-pressure plasma source. This versatile microwave-plasma disinfector has the ability to decontaminate heat-sensitive materials by subjecting them to a microwave-assisted plasma with controlled microwave power. This dual-action, at suitable non-destructive microwave and plasma doses, sterilizes the equipment at a lower temperature with higher effectiveness than either plasma or microwaves alone.

In other embodiments, the present invention provides a microwave-plasma disinfector system comprising: a microwave source and a low-temperature atmospheric-pressure plasma source.

In other embodiments, the present invention provides a microwave-plasma disinfector system wherein the microwave source has multi-feed points.

In other embodiments, the present invention provides a microwave-plasma disinfector wherein the microwave source has variable output power.

In other embodiments, the present invention provides a microwave-plasma disinfector wherein the microwave source has multi-feed points and variable output power.

In other embodiments, the present invention provides a microwave-plasma disinfector having the ability to enable an alternating use of the microwave and plasma sources in pulsed operation, by activating one source at a time for short intervals.

In other embodiments, the present invention provides a microwave-plasma disinfector having the ability to enable a synchronized operating mode where both the microwave and plasma sources are operating simultaneously to enhance the effectiveness of the decontamination process.

In other embodiments, the present invention provides a microwave-plasma disinfector having a dynamic matching network and a microwave power control system to ensure that each source delivers the desired power despite any changes in the object composition.

In other embodiments, the present invention provides a microwave-plasma disinfector having the ability to control the duty cycle in a stop-flow operating mode to maintain a uniform temperature distribution.

In other embodiments, the present invention provides a microwave-plasma disinfector wherein the duty cycle is either a continuous- or pulsed-flow operating mode or a combination thereof and is selected according to the required power level for disinfection/sterilization.

In other embodiments, the present invention provides a microwave-plasma disinfector system having a microwave source that uses two or more horn antennas to achieve uniform energy distribution over the object intended to be disinfected.

In other embodiments, the present invention provides a microwave-plasma disinfector wherein the plasma concentration of the plasma source is adjustable to suit the form and cover the surface area of the specimen.

In other embodiments, the present invention provides a microwave-plasma disinfector system wherein the plasma of the plasma source is steerable in order to cover the entire surface area of the object to be sterilized.

In other embodiments, the present invention provides a microwave-plasma disinfector system wherein the energy density in the microwave beam is controlled to avoid reaching temperature levels that may compromise the structural integrity of the specimen.

In other embodiments, the present invention provides a microwave-plasma disinfector system wherein the temperature levels are controlled to suit the type of specimen being disinfected.

In other embodiments, the present invention provides a microwave-plasma disinfector further including an array of infrared sensors inside a cavity to monitor the temperature distribution during the disinfection process.

In other embodiments, the present invention provides a microwave-plasma disinfector system further including parasitic elements and a reflector to direct the surrounding radiation from being bi-directional to unidirectional.

In other embodiments, the present invention provides a microwave-plasma disinfector system further including a choke that is equal in length to the exciter, is short-circuited, and the redirected signal is shifted by a phase of 180 degrees.

In other embodiments, the present invention provides a microwave-plasma disinfector system wherein for the signal to be added constructively to the original signal, the length of the choke is shorter than $\lambda/2$.

In other embodiments, the present invention provides a microwave-plasma disinfector system wherein the choke is a ring around a circular waveguide.

In other embodiments, the present invention provides a microwave-plasma disinfector system wherein the ring is mechanically supported with a depth of $\lambda/4$ which converts the short circuit at the end of this depth to an open circuit to ensure that the currents are choked at the end and the signal sees this choke as nonexistent.

DETAILED DESCRIPTION OF THE DRAWING

DETAILED DESCRIPTION OF THE INVENTION

Figure 1:
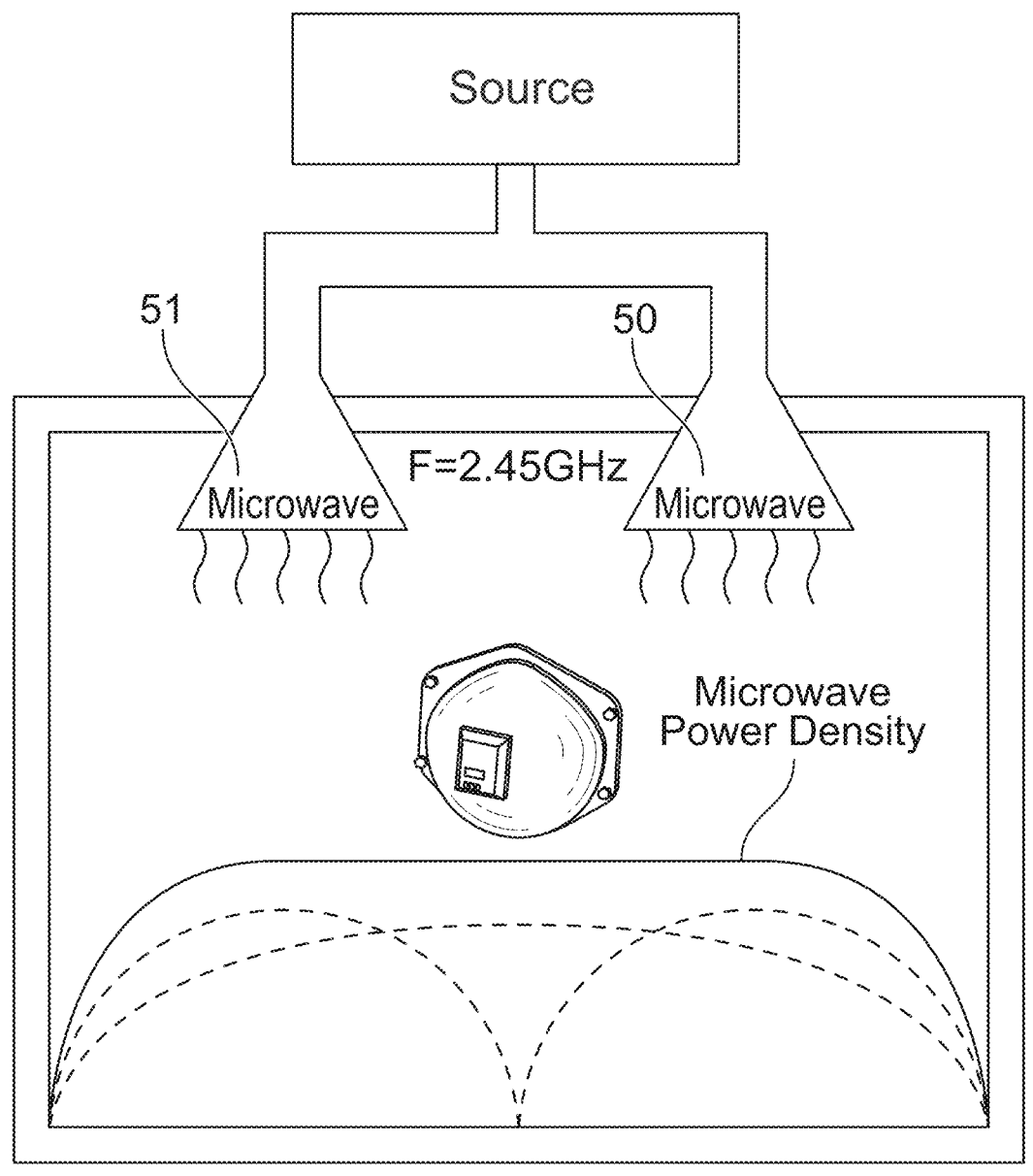
FIG. 1 is a schematic illustration of the effect of the multi-feed microwave system on the uniformity of the power distribution.

Detailed embodiments of the present invention are disclosed herein; however, it is to be understood that the disclosed embodiments are merely exemplary of the invention, which may be embodied in various forms. Therefore, specific structural and functional details disclosed herein are not to be interpreted as limiting, but merely as a representative basis for teaching one skilled in the art to variously employ the present invention in virtually any appropriately detailed method, structure, or system. Further, the terms and phrases used herein are not intended to be limiting, but rather to provide an understandable description of the invention.

In one embodiment, the present invention enables the alternating use of the microwave and plasma sources in pulsed operation, by activating one source at a time for short intervals. This provides significant flexibility in the design and use. A synchronized operating mode may also be enabled where both the microwave and plasma sources are operating simultaneously to enhance the effectiveness of the decontamination process.

The microwave source may work at a 2.4-2.5 GHz frequency range and should be tested to assess its transient and steady-state characteristics. A dynamic matching network and a robust microwave power control system may also be used to ensure that the source delivers the desired power despite any changes in the object composition.

The microwave source may also be operated in a pulsed mode. Controlling the duty cycle in a stop-flow operating mode is important as it extensively affects the uniformity of temperature distribution. Depending on the shape, dimensions, material, and density of the specimen to be disinfected, either a continuous- or pulsed-flow operating mode or a combination of these two modes may be selected according to the required power level for disinfection/sterilization.

An atmospheric-level plasma source may also be used. The capabilities of the plasma source may be used in a continuous mode. It should be noted that due to the expected delicacy of some objects and their susceptibility to being damaged at higher decontamination temperatures, a room-temperature operation is considered for the plasma source. In addition, a pulsed-mode operation of the plasma source may be used.

Optimizing the microwave and plasma feed systems is another consideration. The wavelength of the microwave signal projected to be used in the Microwave-Plasma Disinfector (Origreen) is 12.24 cm in free space. For the range of cavity dimensions expected to be used in the final design, the cavity becomes over-moded and demonstrates non-uniform microwave power density. This results in unpredictable hot and cold spots on the specimen which compromises the effectiveness of the decontamination process. To overcome this drawback, the microwave system of the present invention is designed to split the source power and subsequently inject it into the cavity using two or more horn antennas to achieve uniform energy distribution over the object intended to be disinfected. The exact location and relative phase of each feed point shape the electromagnetic field distribution which helps in achieving the desired uniform microwave spatial power distribution within the "sweet" zone of the cavity.

A schematic representation of this embodiment of the present invention is shown in FIG. 1. For simplicity, only two horn antennas 50 and 51 are shown. However, additional antennas may be added at other locations. Together, they are considered and analyzed as an antenna array.

Figure 2:
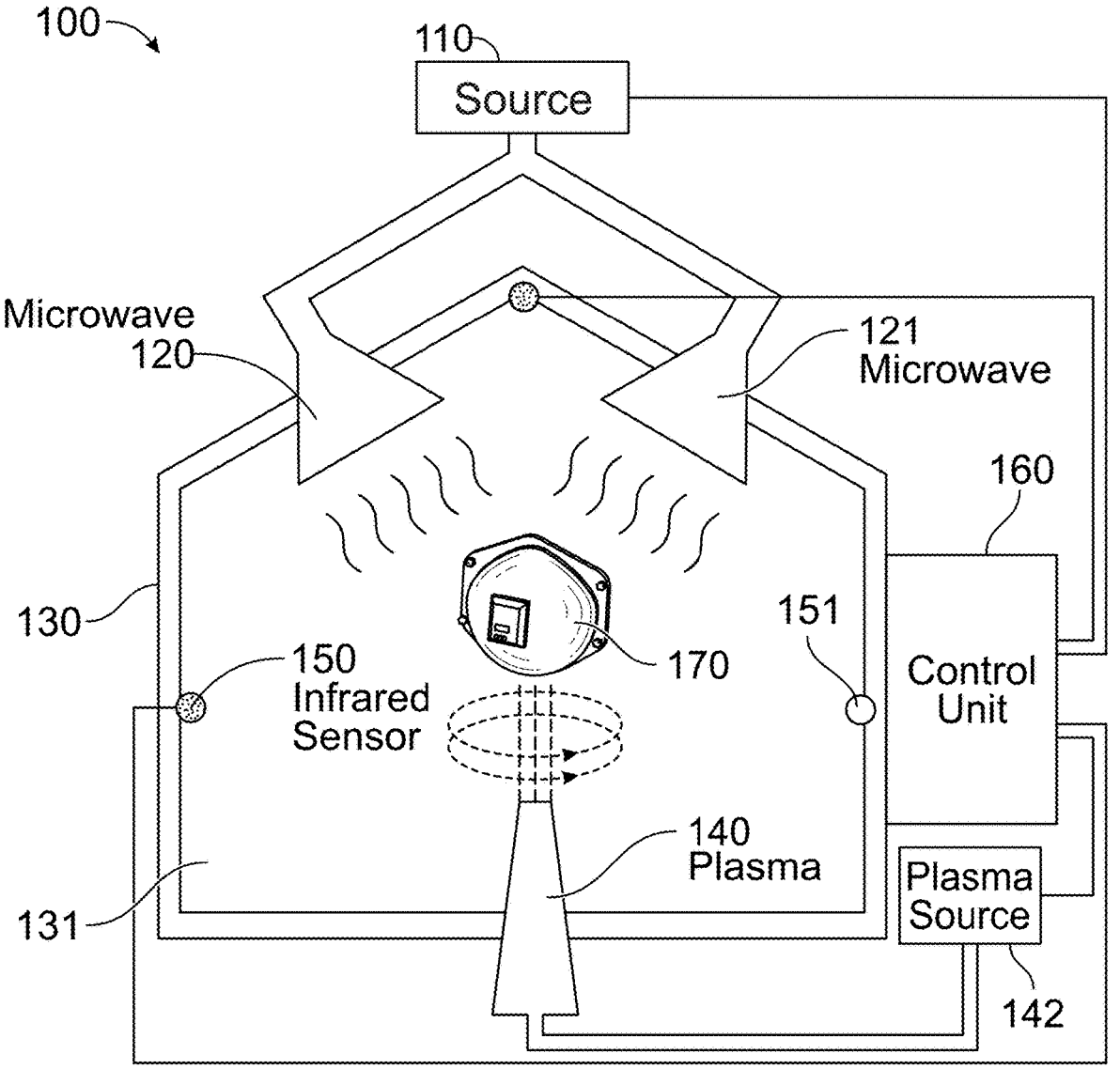
FIG. 2 depicts another embodiment of the present invention.

As shown in FIG. 2, a multi-feed microwave system 100 is adapted to achieve uniformity of the power distribution. Multi-feed microwave system 100 includes source 110, microwave antennas 120 and 121, enclosure 130, plasma jet 140 connected to plasma source 142, and one or more infrared sensors 150 and 151 connected to a control unit 160.

The feed system for plasma jet 140 is optimized as well. A specific concentration may be offered using various spray heads. In general, the plasma jet must be suitable for the object to be disinfected which requires the plasma concentration to be adjustable to suit the form and cover the surface area of specimen 170. Moreover, plasma jet 140 may be adapted to cover the whole surface area of the object to be sterilized.

Adjustments of the beam focus may be accomplished using a magnetic field. This field also provides an opportunity to steer the focused plasma beam at specific angles. Moreover, for objects with a larger surface area, there is a need to steer the beam by changing the position of the plasma source, which requires the nozzle to move.

Other features of the present invention include:

1. Operating with continuous microwave and plasma beams acting simultaneously on the specimen. The energy density in the microwave beam is controlled to avoid reaching temperature levels that may compromise the structural integrity of the specimen. The temperature levels are also controlled to suit the type of specimen being disinfected.

2. The ability to subject the contaminated specimen to successive pulses of high-power microwaves and plasma to have a continued disinfection process without elevating the temperature of the specimen to damaging levels. The duty cycle of the pulsed operation is controlled by control unit 160 as shown in FIG. 2.

3. There are multiple microwave feed points 120 and 121 into cavity 131 to achieve a more uniform power distribution, which results in a more uniform temperature distribution within specimen 170 as shown in FIG. 2.

4. An array of infrared sensors 150 and 151 is also present inside cavity 131 to monitor the temperature distribution during the disinfection process as shown in FIG. 2. Dynamically adjusting the microwave spatial power distributions assists in minimizing the temperature fluctuations induced by variations in the specimen composition.

In other aspects, the present invention includes an optimized circular waveguide with appropriate chokes to achieve the widest beam width, the lowest possible cross-polarization, and the lowest gain.

Figure 3:
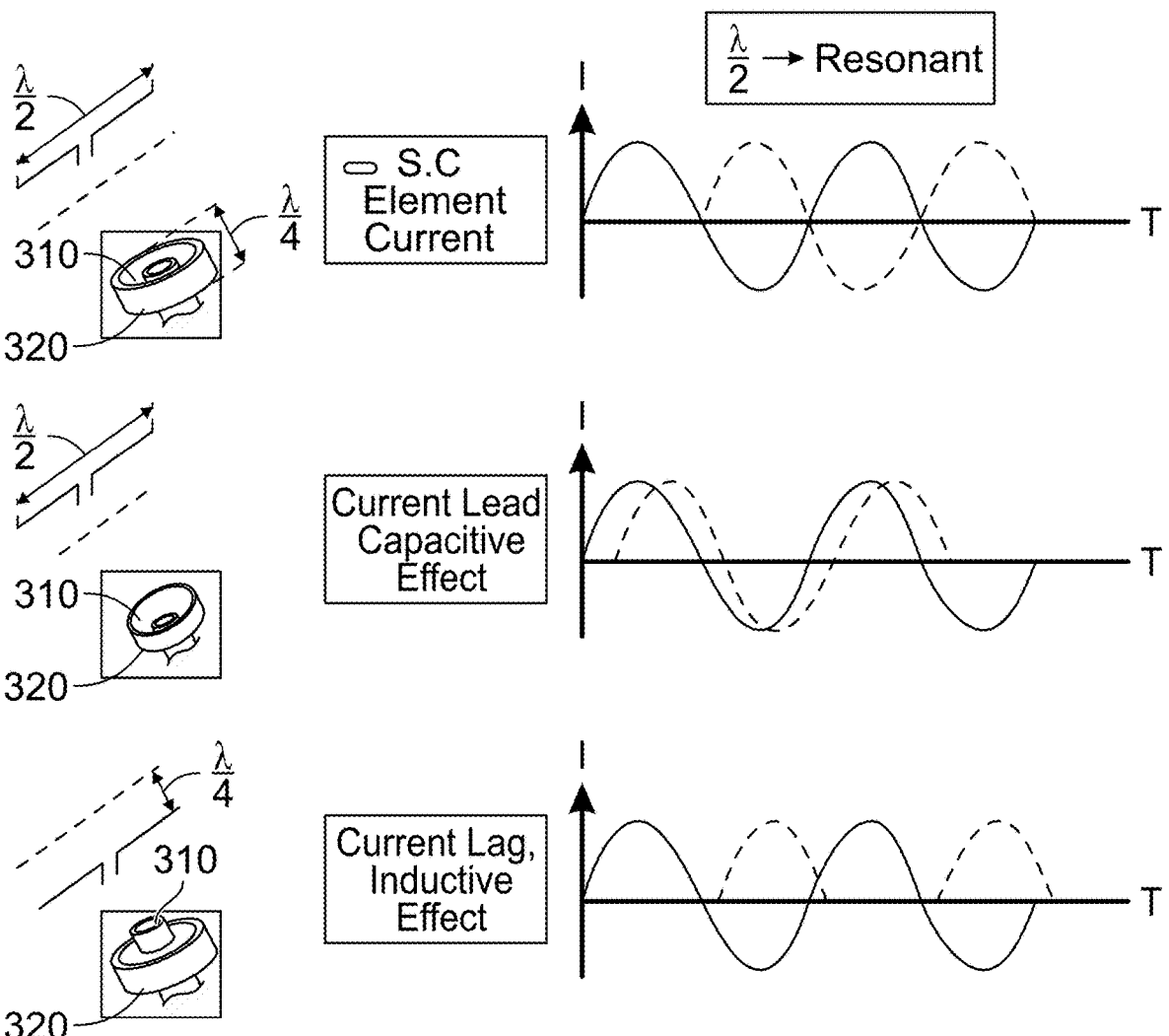
FIGS. 3 and 4 illustrate how the distance between the opening of the circular waveguide and the edge of the choke manipulates the phase of the redirected signal.
Figure 4:
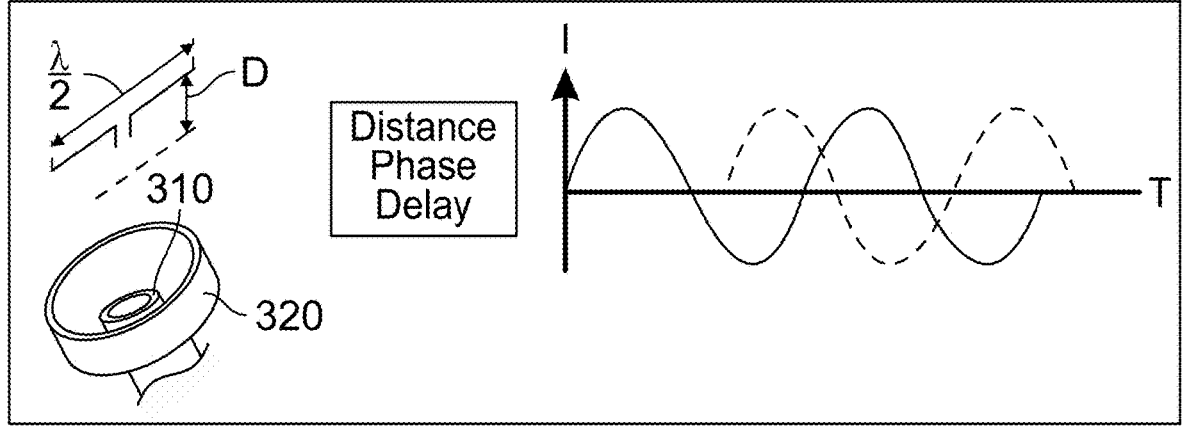
Figure 5:
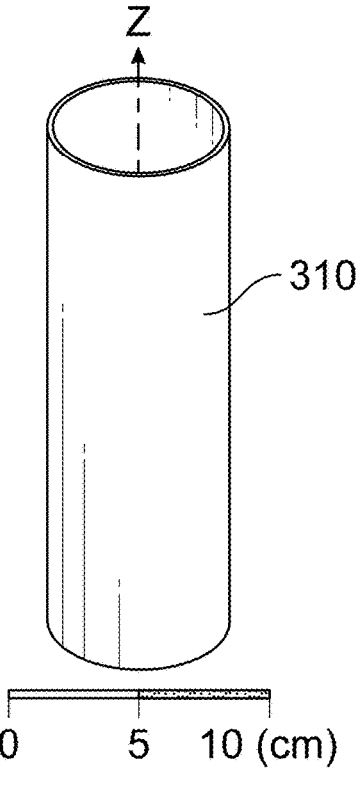
FIGS. 5 and 6 illustrate the resulting signal without a choke.
Figure 6:
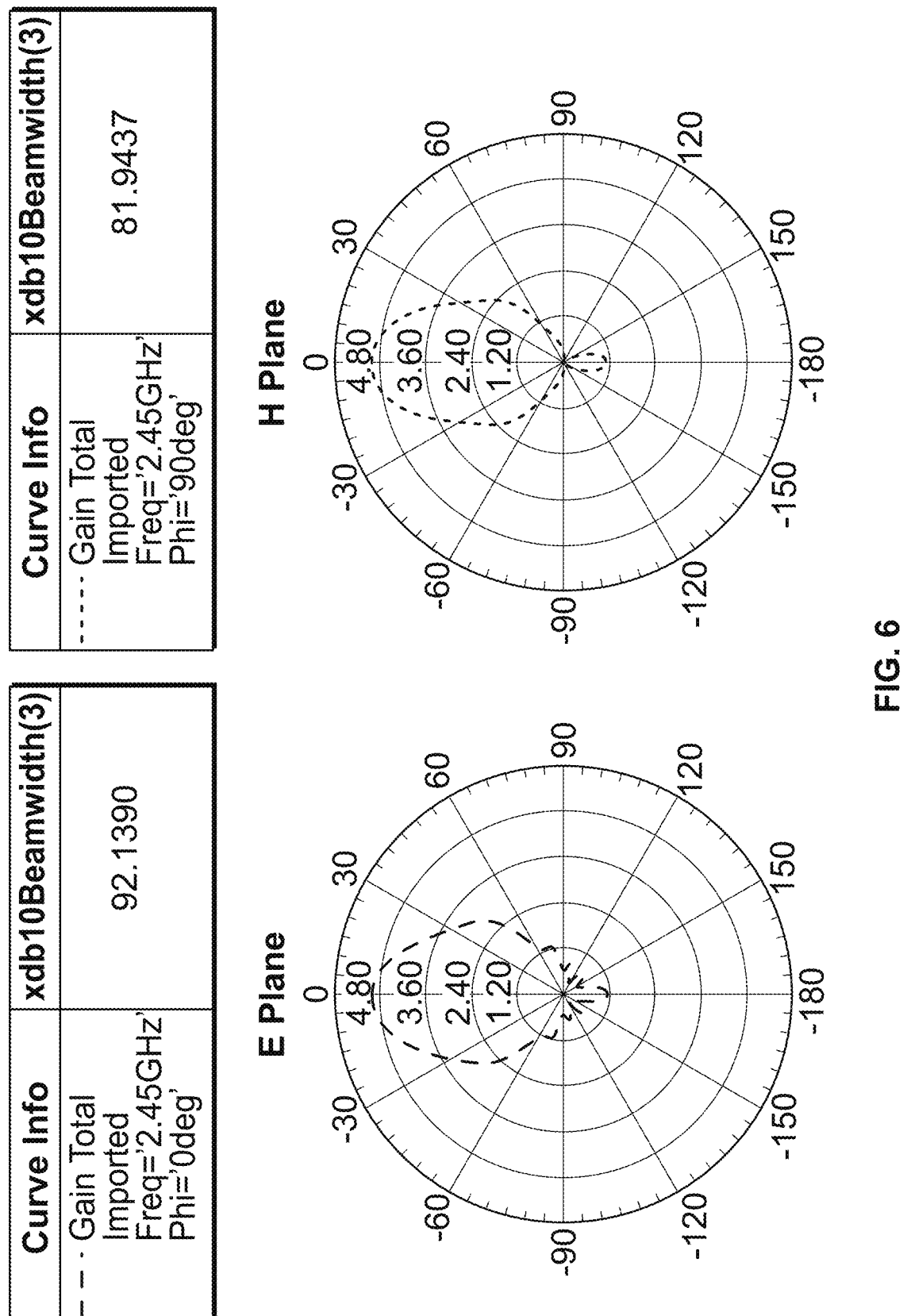
Figure 7:
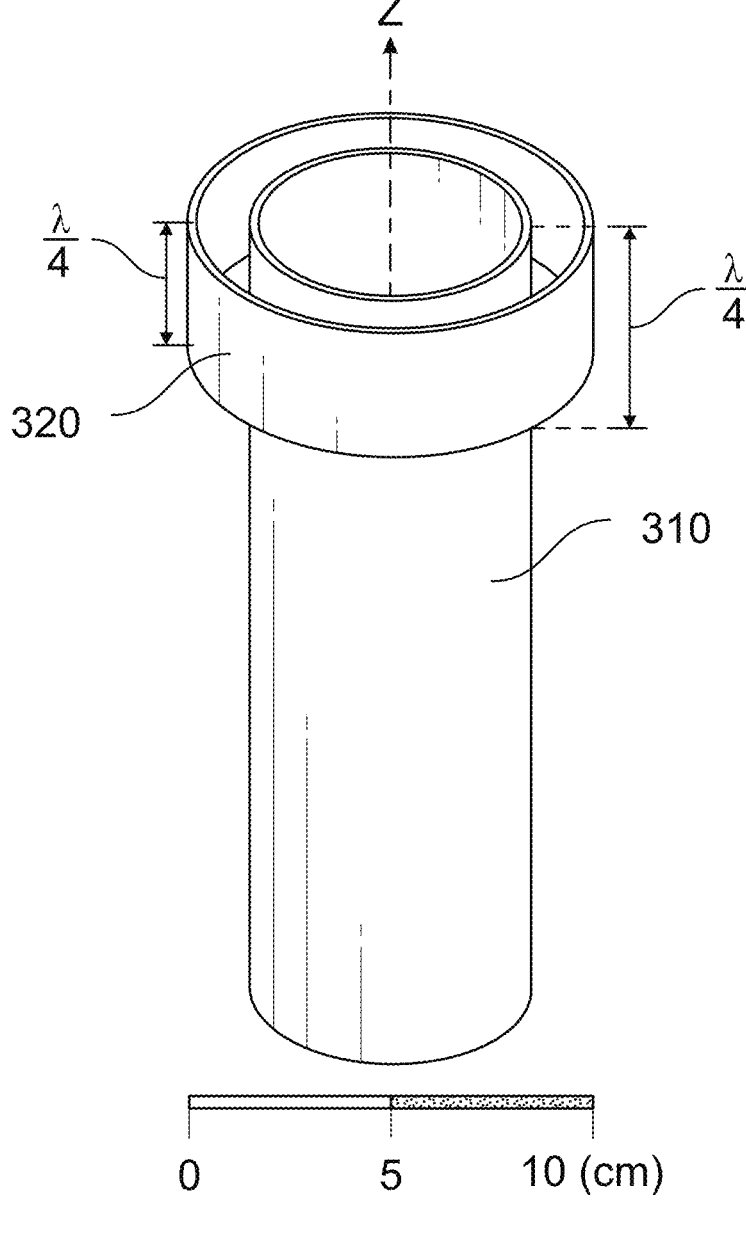
FIGS. 7 and 8 illustrate the resulting signal with a single choke.
Figure 8:
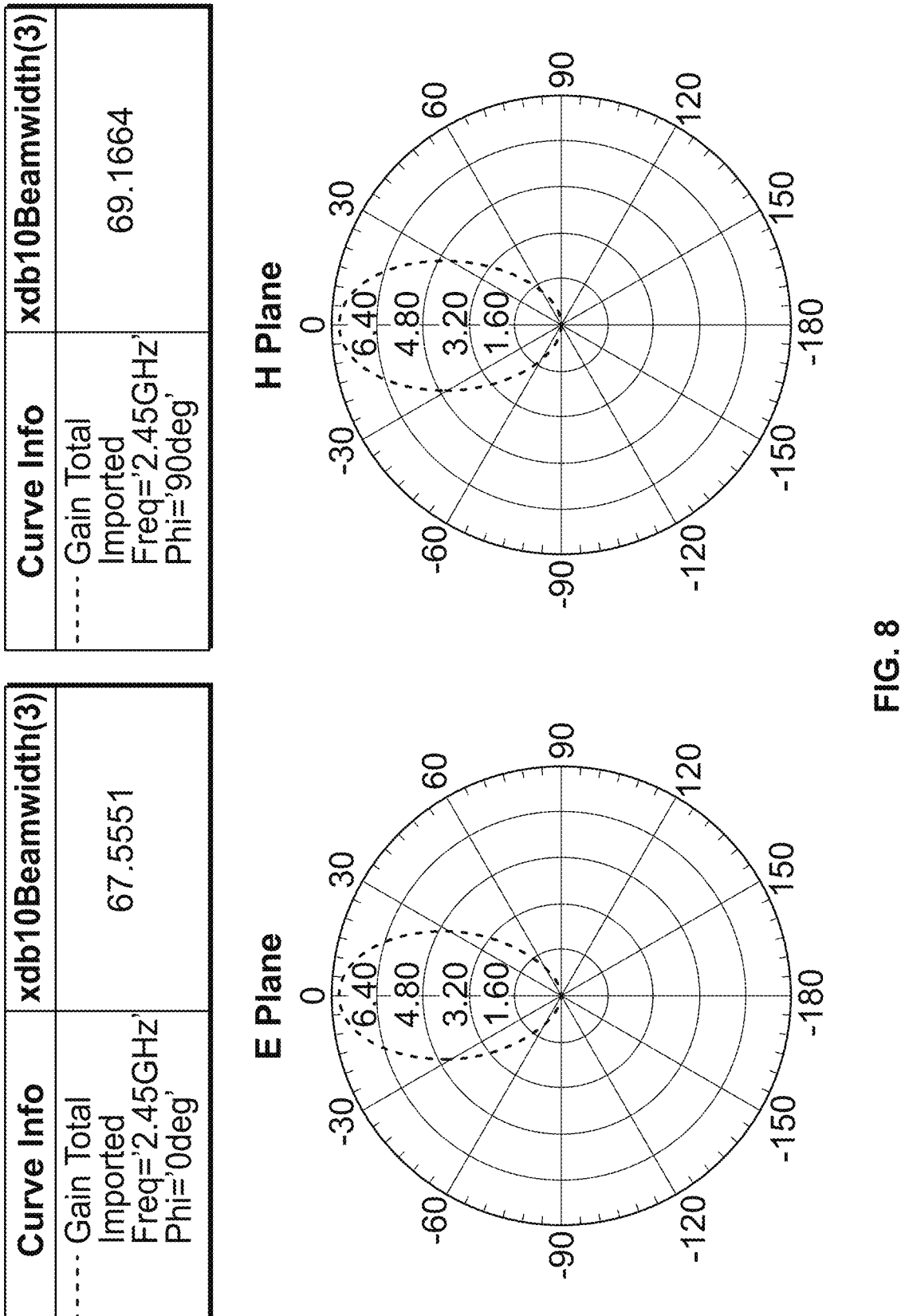

FIGS. 3 and 4 illustrate how the distance between the opening of the circular waveguide 310 and the edge of the choke 320 manipulates the phase of the redirected signal. FIGS. 5 and 6 illustrate the resulting signal without a choke. FIGS. 7 and 8 illustrate the resulting signal with a single choke.

In a preferred embodiment, to direct the surrounding radiation from being bi-directional to unidirectional, several parasitic elements and a reflector are used. In another embodiment, an element such as a choke that is equal in length to the exciter is used and is short-circuited, and the redirected signal that is coming out of this element is shifted by a phase of 180 degrees. For the signal to be added constructively to the original signal, the length of this element must be shorter than $\lambda/2$. This influences the current in this element by a phase lead that depends on the capacitive effect of this length.

In yet other embodiments, choke 320 may be a ring around a circular waveguide 310, which is shorted and can capture the signal and redirect as shown in FIG. 7. This ring is mechanically supported which is done by using a choke with a depth of $\lambda/4$. Quarter wavelength depth converts the short circuit at the end of this depth to an open circuit. This ensures that the currents are choked at this end and the signal sees this choke as nonexistent. The ring may be located in front of the opening of the circular waveguide.

In both antennas, this is the function of the director element. When the opposite is done, current lag results in this case which is the purpose of the reflector. The distance between the opening of the circular waveguide and the edge of the choke manipulates the phase of the redirected signal as well.

Another aspect of the present invention was to evaluate the behavior of the plasma beam in the presence of a microwave signal at a nominal frequency of 2.45 GHz. In other words, numerical simulations were performed to analyze the electromagnetic fields and plasma distributions in the apparatus cavity in the presence of a specimen. The obtained results and the relationship between the microwave intensity and plasma density lead to designing the control unit and the user interface of the disinfector. This unit enables the alternating use of the microwave and plasma sources in pulsed operation, by activating one source at a time for short intervals. This provides significant flexibility in the design and use of the proposed disinfector. A synchronized operating mode is also enabled where both the microwave and plasma sources are operating simultaneously to enhance the effectiveness of the decontamination process.

In other aspects, the present invention provides a dynamic matching network and a robust microwave power control system to ensure that the source delivers the desired power despite any changes in the object composition. Controlling the duty cycle in a stop-flow operating mode affects the uniformity of temperature distribution in samples exposed to microwave radiation. Depending on the shape, dimensions, material, and density of the specimen to be disinfected, either a continuous- or pulsed-flow operating mode or a combination of these two modes may be selected according to the required power level for disinfection/sterilization.

Moreover, as discussed above, an atmospheric-level plasma source is adapted for the disinfector as the other disinfecting component in another embodiment of the present invention. Due to the expected delicacy of some objects and their susceptibility to being damaged at higher decontamination temperatures, a room-temperature operation is considered for the plasma source.

Figure 9:
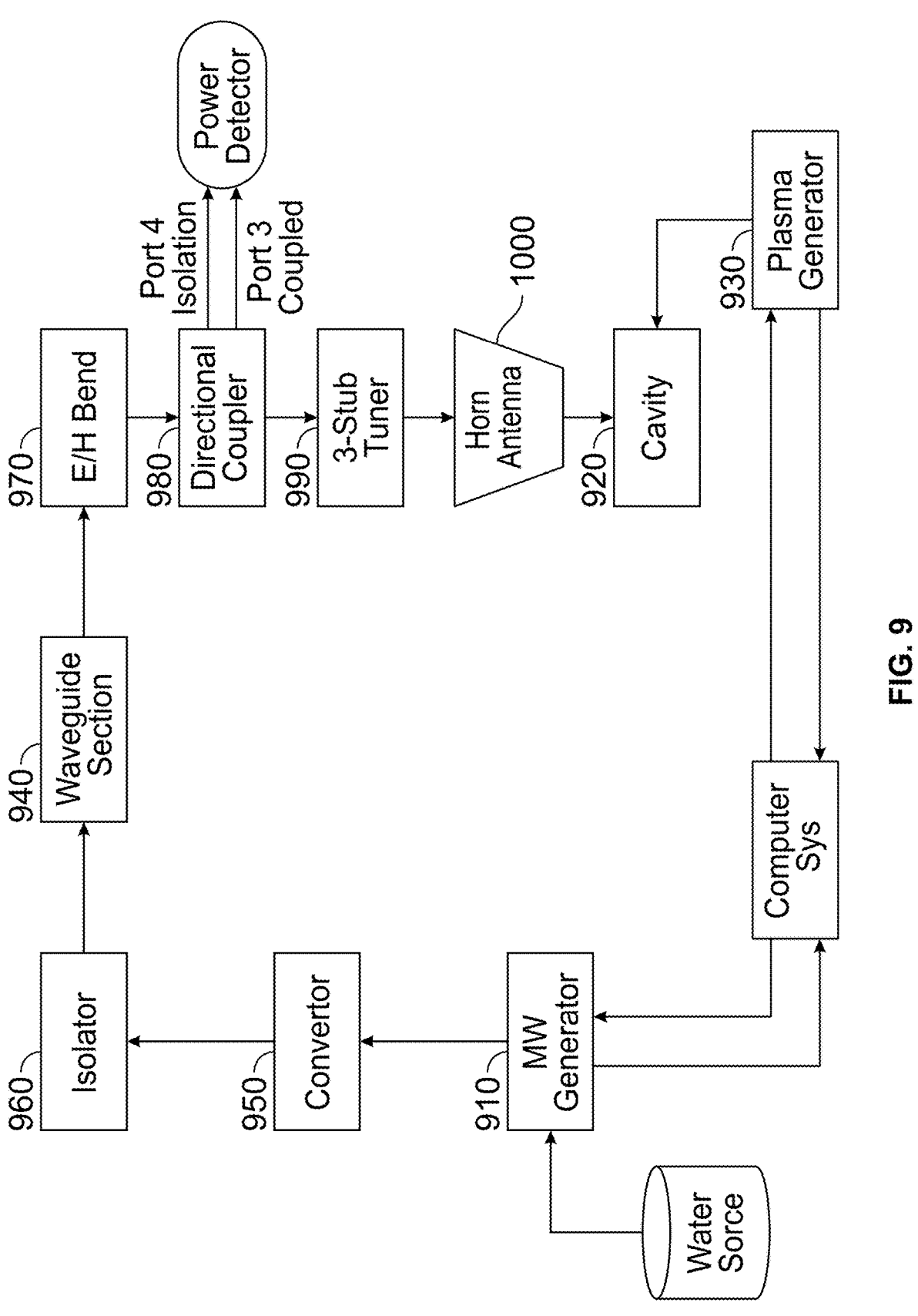
FIG. 9 shows a setup for an embodiment of the present invention.

Important elements in the present invention are the microwave and plasma sources. In order to connect them to the cavity and use them efficiently, a waveguide environment is chosen to deliver microwave power. As shown in FIG. 9, the following are the devices and equipment to be used: 1. Microwave Generator 910: A 1.4 kW solid-state source is chosen due to the flexibility and precision in controlling the power level. The power controllability that the solid-state generator offers is very critical in trying to eliminate unwanted pathogens while keeping the temperature low and the fabric intact in the processed samples. This device employs different modes, namely pulsed and continuous waves. The source operates at a frequency range between 2.4-2.5 GHz. 2. Microwave Cavity 920: A microwave oven is used as the cavity. The oven is cut and modified to accommodate both the microwave antenna and the plasma nozzle. 3. Plasma Source 930: Due to its relevantly low temperature, an atmospheric pressure plasma jet is used to generate the plasma power. This device can provide 1 kW of power. 4. Waveguides 940: A WR-340 waveguide system is utilized. These waveguides are designed to work in the frequency range that the MW generator operates (2.4-2.5 GHz). a. DIN to WR340 Adaptor 950: used to convert from coaxial to the waveguide. b. WR340 3-Port Isolator 960: used to prevent the reflected power from damaging the generator. c. WR340 Straight Rigid Waveguide 940: used to connect different parts of the system. d. WR340 90° E-Bend and H-Bend Waveguides 970: to be able to connect the device with angles without affecting the power. e. WR340 Dual Broadwall Coupler 980: used to be able to measure the reflected power in order to match the system. This coupler has 20 dB directivity. f. WR340 Manual 3 Stub Tuner 990: used to match the source to the load. g. WR340 Horn Antenna 1000: used to direct the power to the sample. 5. Power Meter: A power meter is used to measure the coupled port in the directional coupler.

Figure 10:
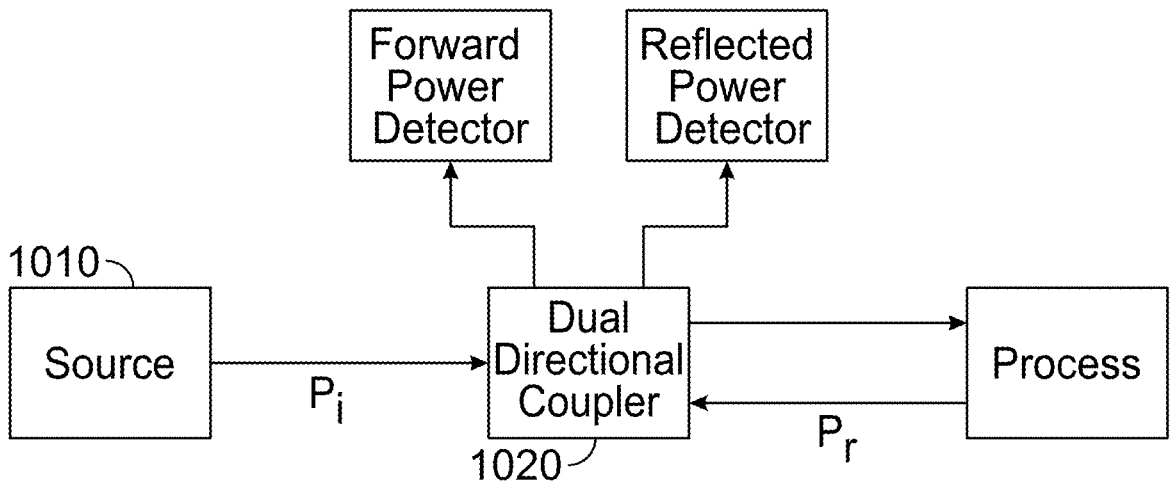
FIG. 10 shows an embodiment of the present invention connected to a series of waveguides to enclose the power and prevent reflections.

FIG. 10 shows another setup where the connection from the plasma device to the cavity is straightforward. However, the MW source 1010 needs to be connected to a series of waveguides to enclose the power and prevent reflections. The incoming power from the source is fed to the load while a small amount is sampled to the coupled port 1020. Depending on the coupling factor, the percentage of power measured at the coupled output will differ. In our case, the coupling factor is 20 dB and for the incoming power of 1.4 kW, the power at the coupled port is 14 W.

Figure 11:
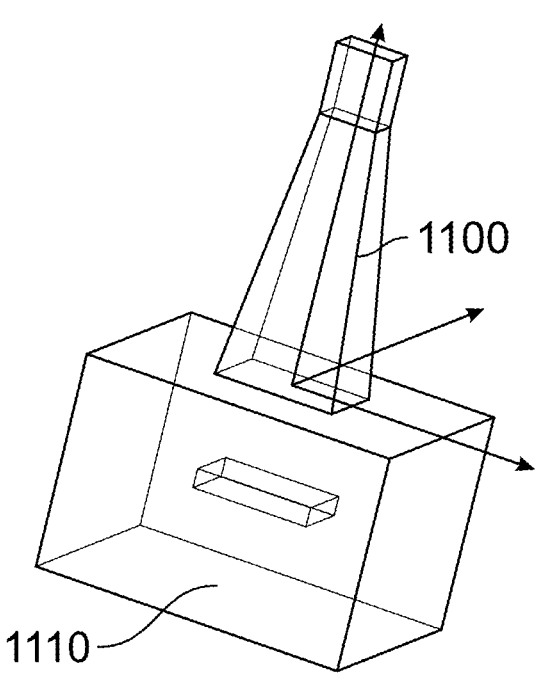
FIG. 11 shows an antenna and cavity design for an embodiment of the present invention.

In order to see the power distribution results inside the microwave cavity and, more importantly, on the specimen, an analysis was conducted in HFSS. The analysis starts with defining the configuration of the antenna 1100 and cavity 1110 as shown in FIG. 11. The waveguide structure to be operated at 2.4 GHz is connected to the horn antenna. The antenna aperture is then connected to the cavity, where the specimen is considered to be placed. The input source is applied to the waveguide and the power distribution is observed on the specimen. According to the dimensions, there is an over-moded cavity and obtaining the desired accurate results requires the analysis to go through a large number of iterations, with different antenna configurations, phase differences, and input power values. The dimensions for all the introduced components in FIG. 11 are presented in Table 1. The dimensions of the specimen are set to be equal to a disposable face mask.

TABLE 1

| Name | Evaluated Value (in) |
|---|---|
| Horn height | 15 |
| Long flare | 7 |
| Short Flare | 5 |
| Waveguide length | 3.4 |
| Waveguide width | 1.7 |
| Waveguide height | 4 |
| Cavity length | 18 |
| Cavity width | 14 |
| Cavity height | 12 |
| Specimen length | 6.75 |
| Specimen width | 3.75 |
| Specimen height | 0.1 |

Figure 12B:
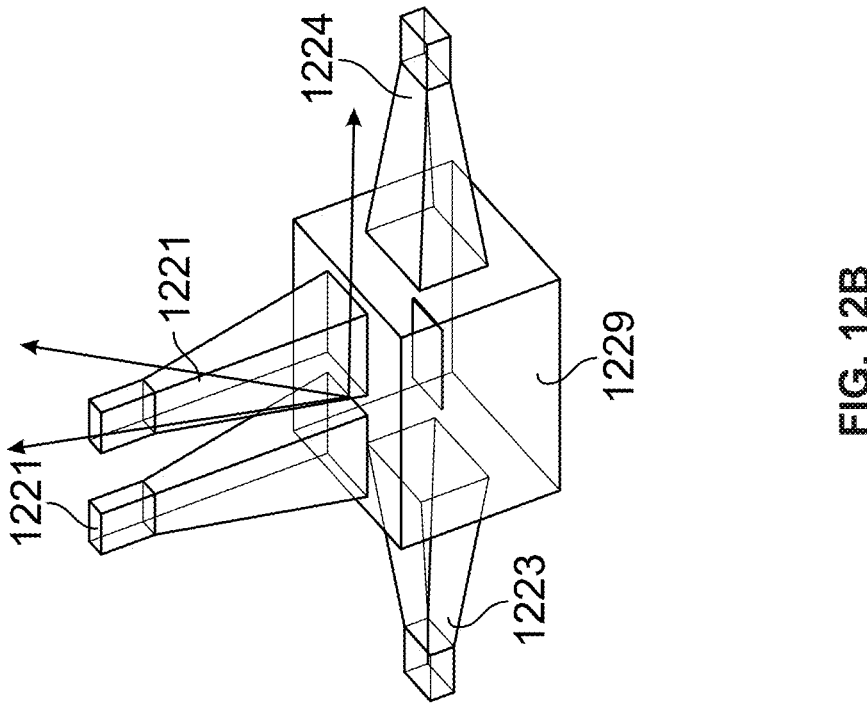
FIGS. 12A and 12B show the antenna and cavity design to achieve maximum uniformity of the power distribution on the specimen for an embodiment of the present invention.
Figure 12A:
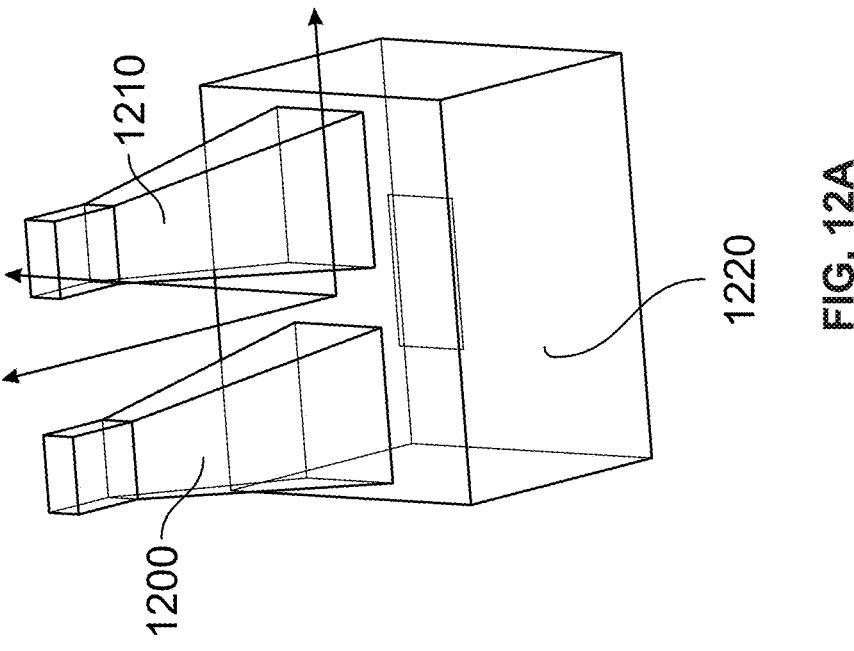

Other than the configuration presented in FIG. 11, some other antenna configurations may be used to ensure the maximum uniformity of the power distribution on the specimen. Two of these configurations are provided in FIGS. 12*a* and 12*b*. FIG. 12*a* shows two horn antennas 1200 and 1210 feeding cavity 1220 where both antennas are adjacent and on one side of the cavity. FIG. 12*b* shows four horn antennas 1221-1223 feeding cavity 1229 where two antennas are adjacent and on one side of the cavity and two antennas are opposing located. It is worth noting that when the final results from all these options are compared, the total input power is equal for all the cases.

Figure 13A:
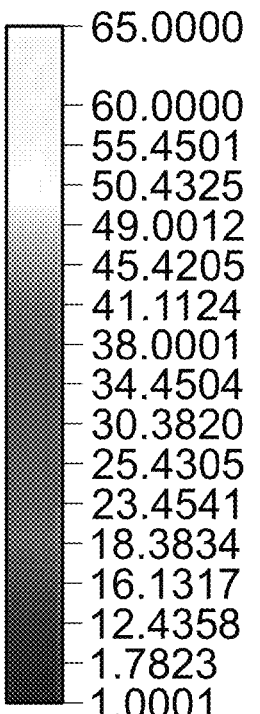
FIGS. 13A and 13B show the results achieved for different embodiments of the present invention.
Figure 13A:
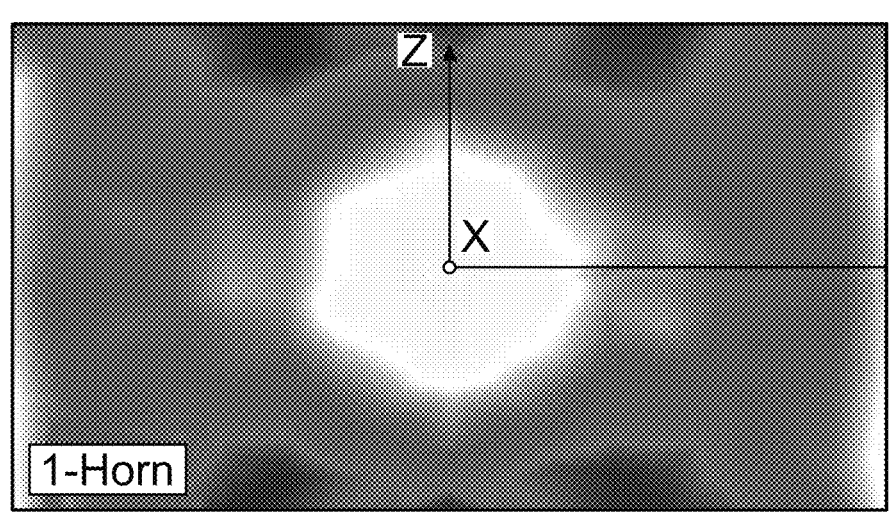
Figure 13A:
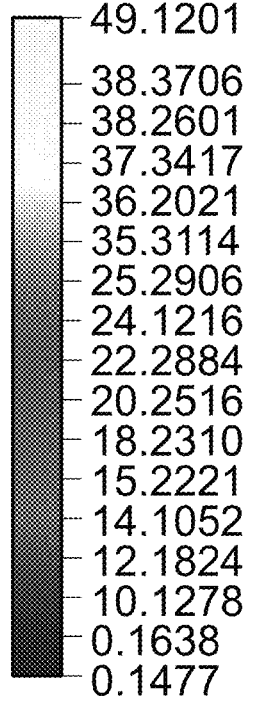
Figure 13A:
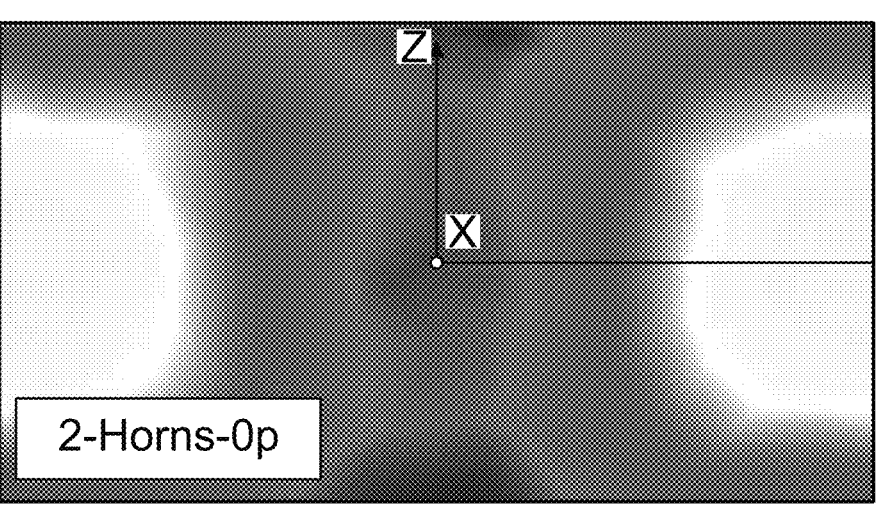
Figure 13A:
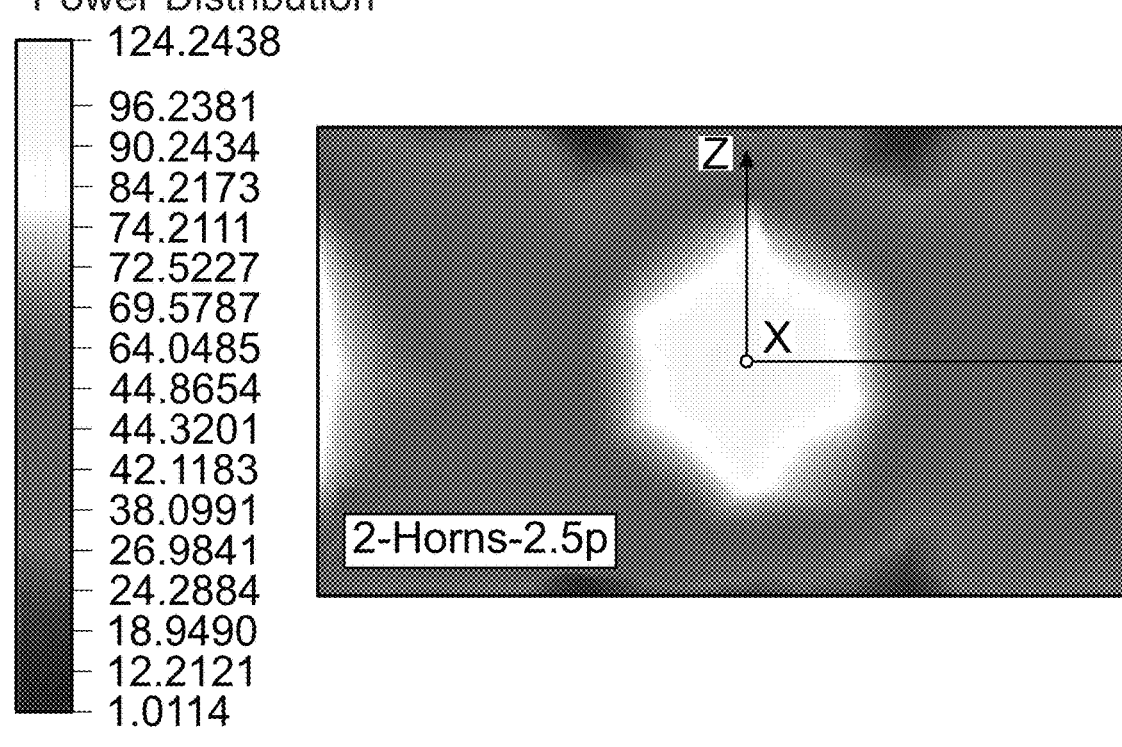
Figure 13A:
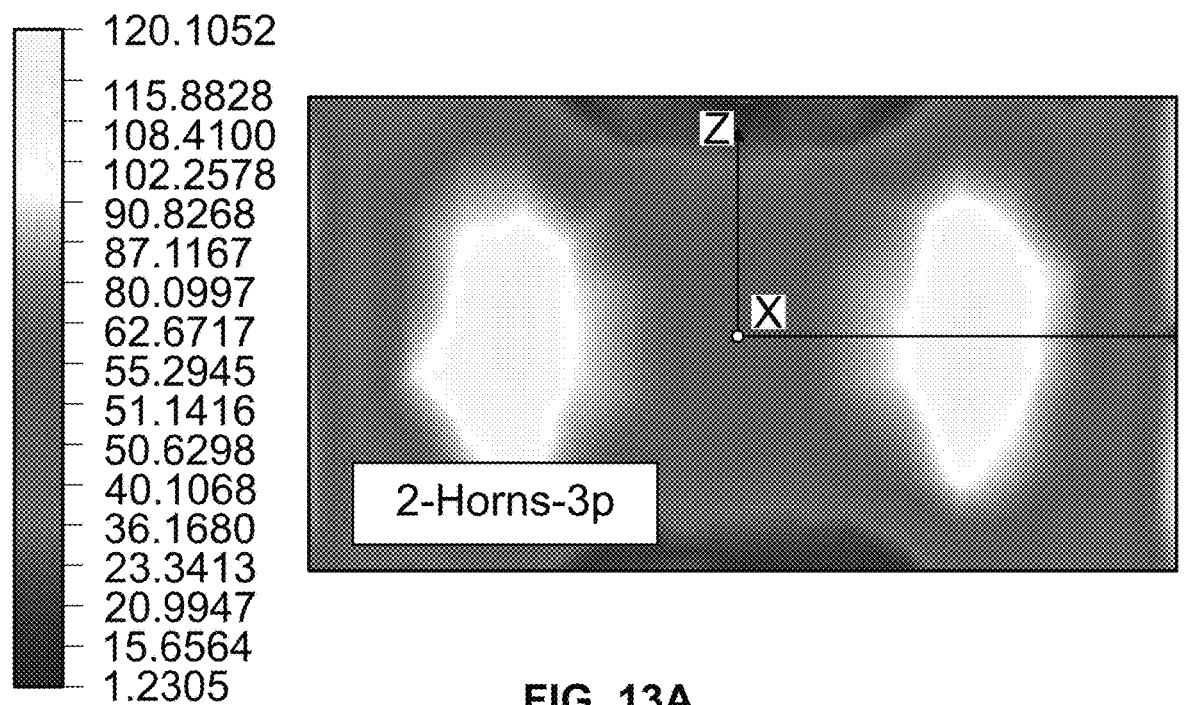
Figure 13B:
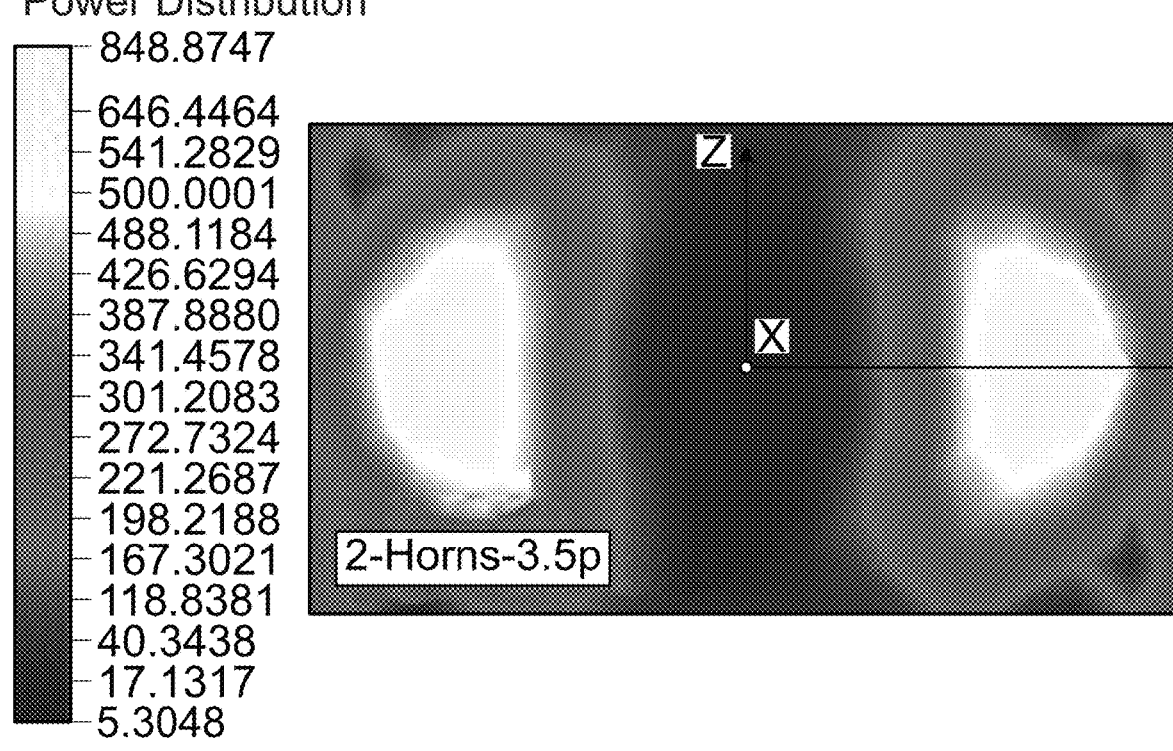
Figure 13B:
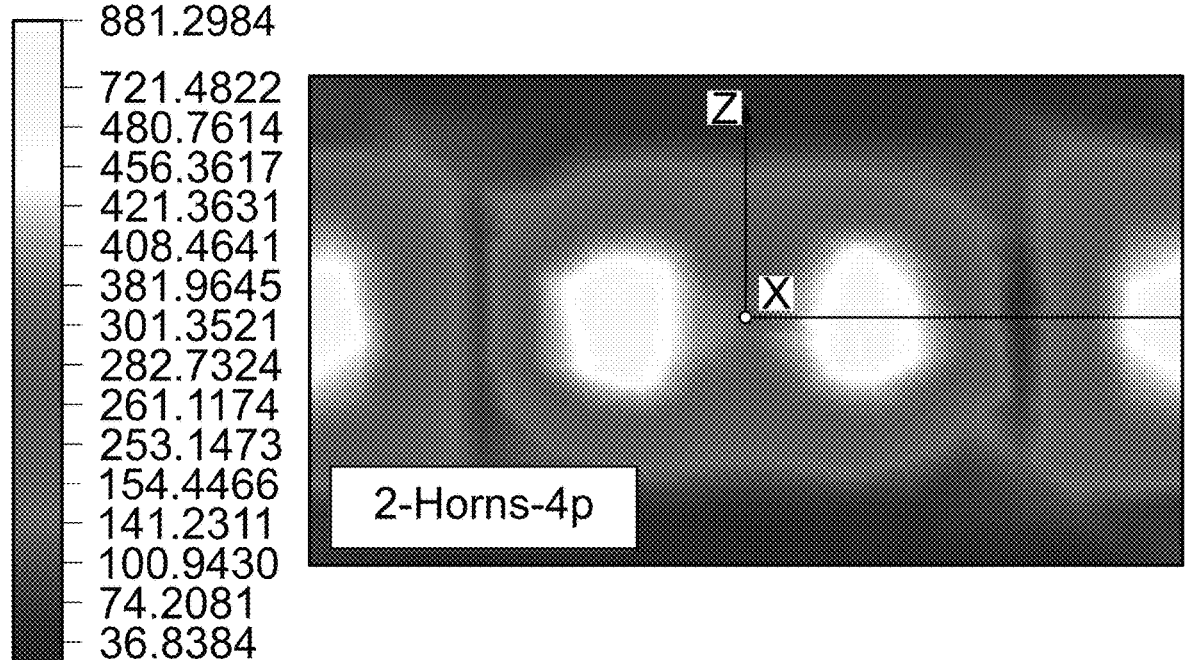
Figure 13B:
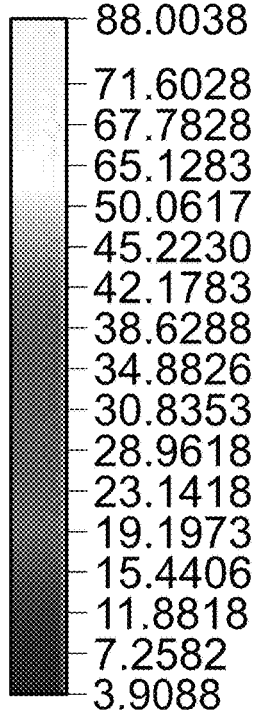
Figure 13B:
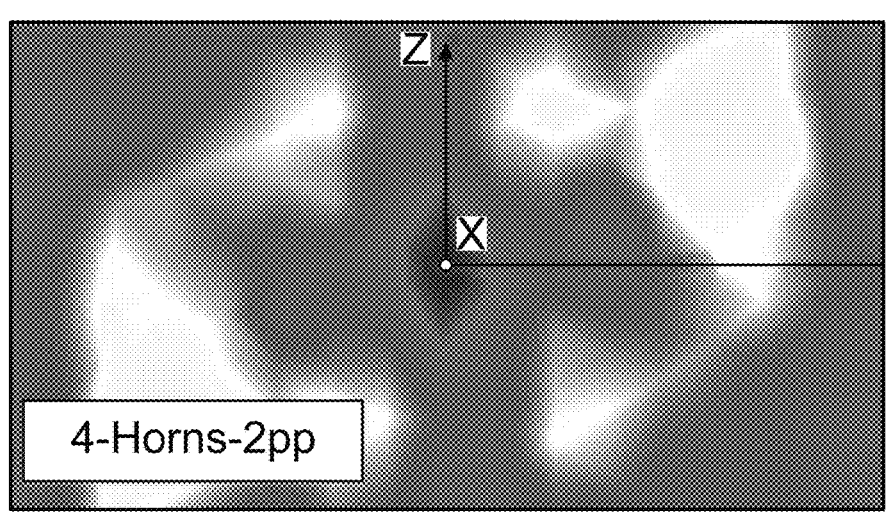
Figure 13B:
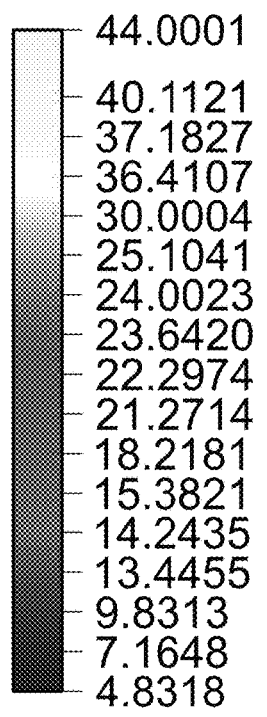
Figure 13B:
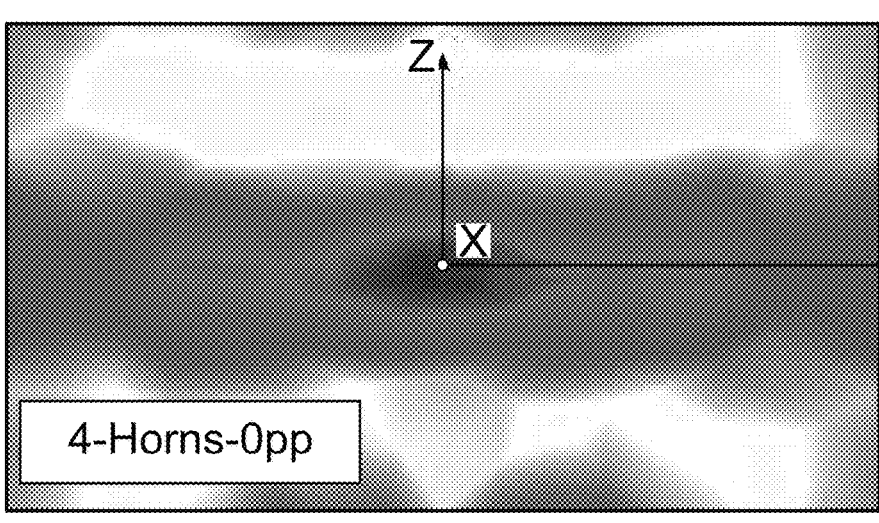

One of the elements that had a significant effect on the final results was the distance between the two antennas placed on top of the cavity. After analyzing all antenna configurations with the required iterations, the power distribution results on the specimen (face mask) were obtained. FIGS. 13*a*-13*b* show some of the results achieved for different structures. The specified number before "horn" shows the number of antennas according to the presented configurations in FIGS. 11, 12*a*, and 12*b*, and the number after that is the distance between the antenna walls on top of the cavity in inches. Also, "p" represents the fact that the two antennas attached to the top of the cavity are out-of-phase or there is a phase difference of 180 degrees between them, and "pp" denotes the case for out-of-phase antennas on the side for the case with 4 different horn antennas. In order to decide on the best results obtained, other than the observable components, a scientific method is also utilized. The mean and standard deviation value was obtained for all the results as presented in Table 2.

TABLE 2

| Configuration | Mean | Standard Deviation |
|---|---|---|
| 1-horn | 35.4 | 12.7 |
| 2-horns-0p | 23.7 | 8.3 |
| 2-horns-2.5p | 58.2 | 17.6 |
| 2-horns-3p | 74.8 | 30.2 |
| 2-horns-2.5p | 244.0 | 185.3 |
| 2-horns-4p | 198.7 | 149.1 |
| 4-horns-0pp | 28.9 | 7.5 |
| 4-horns-2pp | 38.9 | 11.9 |

Accordingly, the three cases with the lowest values of standard deviation values are considered to be more effective when the point of comparison is the uniformity of the power distribution. Additionally, rotating the specimen in different directions finally leads to better uniformity.

While the foregoing written description enables one of ordinary skill to make and use what is considered presently to be the best mode thereof, those of ordinary skill will understand and appreciate the existence of variations, combinations, and equivalents of the specific embodiment, method, and examples herein. The disclosure should therefore not be limited by the above-described embodiments, methods, and examples, but by all embodiments and methods within the scope and spirit of the disclosure. Also, to the above description, the materials attached hereto form part of the disclosure of this provisional patent application.

What is claimed is:

1. A microwave-plasma disinfector system comprising:
   An exciter comprised of a microwave source and an atmospheric-pressure plasma source; and
   a choke that is equal in length to said exciter, is short-circuited, and generates a redirected signal that is shifted by a phase of 180 degrees.

2. The microwave-plasma disinfector system of claim 1 wherein the microwave source has multi-feed points.

3. The microwave-plasma disinfector system of claim 1 wherein the microwave source has variable output power.

4. The microwave-plasma disinfector system of claim 1 wherein the microwave source has multi-feed points and variable output power.

5. The microwave-plasma disinfector of claim 1 having the ability to enable an alternating use of the microwave and plasma sources in pulsed operation, by activating one source at a time for short intervals.

6. The microwave-plasma disinfector system of claim 1 having the ability to enable a synchronized operating mode where both the microwave and plasma sources are operating simultaneously to enhance the effectiveness of the decontamination process.

7. The microwave-plasma disinfector system of claim 1 having a dynamic matching network and a microwave power control system to ensure that each source delivers a predetermined amount of power despite any changes in the object composition.

8. The microwave-plasma disinfector system of claim 1 having the ability to control a duty cycle in a stop-flow operating mode to maintain a uniform temperature distribution.

9. The microwave-plasma disinfector of claim 8 wherein the duty cycle is either a continuous-or pulsed-flow operating mode or a combination thereof and is selected according to the required power level for disinfection/sterilization.

10. A microwave-plasma disinfector system comprising:

A cavity adapted to receive an object to be disinfected;

An exciter comprised of a microwave source and an atmospheric-pressure plasma source; and A choke that is equal in length to said exciter, is short-circuited, and generates a redirected signal that is shifted by a phase of 180 degrees; and Wherein said microwave source uses two or more horn antennas to achieve uniform energy distribution over the object located in said cavity; and an array of infrared sensor located inside said cavity to monitor the energy distribution in said cavity during the disinfection process.

11. The microwave-plasma disinfector system of claim 10 wherein the plasma concentration of the plasma source is adjustable.

12. The microwave-plasma disinfector system of claim 10 wherein the plasma of the plasma source is steerable in order to cover the entire surface area of the object to be sterilized.

13. The microwave-plasma disinfector system of claim 10 wherein the energy density in the microwave beam is controlled to avoid reaching temperature levels that may compromise the structural integrity of the specimen.

14. The microwave-plasma disinfector system of claim 10 wherein the temperature levels are controlled to suit the type of specimen being disinfected.

15. The microwave-plasma disinfector system of claim 1 further including passive conductive elements configured to reflect or direct electromagnetic radiation.

16. The microwave-plasma disinfector system of claim 1 wherein the length of said choke is shorter than $\lambda/2$.

17. The microwave-plasma disinfector system of claim 1 wherein said choke is a ring around a circular waveguide.

18. The microwave-plasma disinfector system of claim 17 wherein said choke ring is mechanically supported with a depth of $\lambda/4$ which converts said short circuit to an open circuit.

\* \* \* \* \*